United States Patent [19]

Sampson

[11] Patent Number: 5,057,326

[45] Date of Patent: * Oct. 15, 1991

[54] FUNGICIDES

[76] Inventor: Michael J. Sampson, 18 Christchurch Road, Norwich, Norfolk NR2 2AE, England

[ * ] Notice: The portion of the term of this patent subsequent to Jul. 25, 2006 has been disclaimed.

[21] Appl. No.: 336,806

[22] Filed: Apr. 12, 1989

Related U.S. Application Data

[63] Continuation-in-part of Ser. No. 127,231, Dec. 1, 1987, Pat. No. 4,851,223, which is a continuation of Ser. No. 718,864, Apr. 2, 1985, abandoned.

[30] Foreign Application Priority Data

Apr. 13, 1988 [GB] United Kingdom ................. 8808646

[51] Int. Cl.$^5$ ...................... A01N 37/00; A01N 59/02
[52] U.S. Cl. .................................... 424/711; 424/713; 514/557
[58] Field of Search ................. 424/711, 713; 514/557

[56] References Cited

U.S. PATENT DOCUMENTS

| | | | |
|---|---|---|---|
| 1,614,063 | 1/1927 | Frazier | 424/162 |
| 3,592,910 | 7/1971 | Clark | 424/300 |
| 3,928,577 | 12/1975 | Kochurova et al. | 424/162 |
| 4,447,798 | 5/1984 | Sampson et al. | 71/92 |
| 4,500,517 | 2/1985 | Luss | 424/162 |

FOREIGN PATENT DOCUMENTS

| | | |
|---|---|---|
| 162551 | 11/1985 | European Pat. Off. . |
| 618351 | 3/1927 | France . |
| 2422331 | 9/1979 | France . |
| 54-37540 | 10/1980 | Japan ................................. 424/162 |
| 8002360 | 11/1980 | PCT Int'l Appl. . |
| 780845 | 12/1978 | South Africa . |

OTHER PUBLICATIONS

Gaur et al; CA. vol. 99 (1983) 99: 193,390.
Singh et al; C. A. vol. 99 (1983) 99: 189,613k.
Sabel'nikova et al, C. A. vol. 73 (1920) 34100c.
Merck Index, 10th Ed. (183) #8411; #8511.
C. R. Worthing, Ed., The Pesticides Manual, 7th Ed., Suffolk, England, 1983, p. 523, item 11500.
W. Perkow, Wirksubstanzen der Pflanzenschutz- und Schadlingsbekampfungsmittel, Berlin and Hamburg, 1982, Fung.-Diphenyl (Biphenyl).

*Primary Examiner*—Allen J. Robinson
*Attorney, Agent, or Firm*—Renner, Otto, Boisselle & Sklar

[57] ABSTRACT

This invention provides for a method of combating fungi on plant material comprising applying to said plant material a fungicidally effective amount of at least two non-toxic water-soluble fungicidal compounds selected from the group consisting of metabisulphites, propionates and sorbates. Fungicidal compositions comprising at least two of said fungicidal compounds are also provided.

16 Claims, No Drawings

FUNGICIDES

This is a continuation-in-part of U.S. application Ser. No. 127,231, filed Dec. 1, 1987, issued as U.S. Pat. No. 4,851,223, which is a continuation of U.S. application Ser. No. 718,864, filed Apr. 2, 1985, now abandoned. The disclosures in these prior applications are incorporated by reference in their entirety in this application.

The present invention relates to fungicides. More particularly, but not exclusively, it is concerned with the use of the three known fungicidal materials sodium metabisulphite, sodium propionate and potassium sorbate, and of other corresponding non-toxic alkali metal (e.g. potassium and sodium) and other non-toxic water-soluble salts.

The present invention is based on the discovery that, while higher concentrations of the individual fungicides are more effective than lower concentrations, the application of more than one of the foregoing fungicides produces a greater fungicidal effect than the sum of the effects of the fungicides if applied separately in the same concentration. Improving the effectiveness in a synergistic manner improves control and cost effectiveness not only when the disease is known to be susceptible to these materials but also where a disease is not susceptible to a single material at commercially acceptable rates.

The invention therefore provides a method of killing fungi on plant material including growing plants and stored crops, comprising applying to the plant material a non-toxic water-soluble metabisulphite, non-toxic water-soluble propionate, and/or a non-toxic water-soluble sorbate, where "non-toxic" means "non-toxic to the plant material and to humans and other animals". Preferred pairs of materials are sodium metabisulphite and sodium propionate, sodium metabisulphite and potassium sorbate, and sodium propionate and potassium sorbate.

Among plant materials that can be protected for storage by the method of the present invention are fruits, non-limiting examples of which are citrus fruits, including oranges, lemons, grapefruits, tangerines, clementines and satsumas, bananas, apples, pineapples, peaches, kiwi fruit, and berries, particularly strawberries but also raspberries, gooseberries, loganberries, tayberries and blackberries; tomatoes, potatoes, celery, mushrooms, carrots, asparagus, lettuce, watercress, brassicas such as cabbages, cauliflowers, broccoli and brussells sprouts, green beans such as French and runner beans, and green peas including petit pois. The materials may be whole or cut or broken up ready for use in a salad or fruit salad. The invention is of particular interest in the storage of potatoes.

In its application to growing plants, any that are subject to fungal attack, including ornamental plants, fruits, vegetables and cereals, may be treated in accordance with the present invention. The rate of application to growing plants may be from 50 to 2500 g/ha of each active ingredient, the concentration being from 0.0125% to 2.5% on a w/v basis: for stored products the concentration is 0.1 to 10% w/v, i.e. 1 to 100 g/l.

The fungicides may be applied, particularly to growing crops, in conjunction with a coating agent such as di-1-p-menthene and its polymers and/or a surface-active agent such as a condensate of nonylphenol ethylene oxide.

The preferred coating agent that can be used in accordance with the invention is di-1-p-menthene (which normally occurs in association with its polymers). Other monoterpenes ($C_{10}H_{16}$) can also be used. The agents can be used in admixture with one another.

Apart from monoterpenes, the following compounds are suitable, though this is not an exhaustive list:
1. Terpene hydrocarbons of the elementary composition $C_{15}H_{24}$ (sesquiterpenes)
2. Terpene hydrocarbons of the elementary composition $C_{20}H_{32}$ (diterpenes)
3. Terpene hydrocarbons of the elementary composition $C_{30}H_{48}$ (triterpenes)
4. Terpenes having 40 carbon atoms (tetraterpenes)
5. Bicyclic and tricyclic monoterpenes and their derivatives (e.g. oxygenated derivatives) such as and pinene, d-camphor, d-borneol, d-tanacetone, $\beta$-thujone, d-$_3$-carene
6. Terpene resins (compounded with or without natural or synthetic rubbers)
7. Gum turpentine
8. Sulphate of turpentine
9. Wood turpentine
10. Pineoils
11. Terpineols
12. Non-oxidizing Alkyd Resins, e.g. those of the castor oil, coconut oil, hydrogenated castor oil, lauric acid, oil-free, saturated acid and synthetic fatty acid types
13. Oxidizing Alkyd Resins, e.g. acrylic-resin-modified dehydrated castor oil types, epoxide-resin-modified, isophthalic-acid-based types, linoleic-rich oil type, linseed oil types, linseed oil/dehydrated castor oil types, linseed oil/soya bean oil types, linseed oil/tung oil types, maleic-resin-modified, marine oil types, phenolic-resin-modified, rosin-modified, safflower seed oil types, silicone-resin-modified, soya bean oil types, soya bean oil/tung oil types, styrenated types, sunflowerseed oil types, tall oil types, tobaccoseed oil types, unmodified types, vinyltoluene-modified types and water-soluble types
14. Benzoguanamine resins
15. Styrene polymers and compolymers, e.g. polystyrene and styrene/maleic anhydride and butadiene/styrene copolymer resins
16. Carbamide resins
17. Copal ester resins
18. Coumarone-indene resins
19. Cresylic resins
20. Epoxy resins- e.g. dehydrated castor oil types, linseed oil types, linseed oil/rosin types, phenolic-resin-modified, soya bean oil types, styrenated types, vinyltoluene-modified, and unmodified types as well as those sold under the trade marks Epikote 205, Epikote 825, Epikote 828 and Epikote 1001
21. Epoxide melamine condensates
22. Epoxide phenolic condensates
23. Ester gums
24. Fumaric resins
25. Furan resins
26. Ketone resins
27. Maleic resins
28. Melamine resins—e.g. butylated types, hexamethoxymethyl types and formaldehyde condensates
29. Metallic rosinates—e.g. calcium or zinc resinates, zinc/calcium mixtures both rosin or modified rosin
30. Phenolic resins and modified phenolic resins—e.g. phenol/aldehyde resole condensates adducted to rosin or modified rosin, as well as phenol/formaldehyde resins
31. Phenoxy resins
32. Polybutadiene resins
33. Polybutene resins
34. Polycarbonate resins
35. Polyisobutylene resins
36. Polyester resins—e.g. polyacrylate and polymethacrylate ester resins
37. Polysulphide resins
38. Polyurethane resins—e.g. modified types and oil-modified types
39. Polyvinyl acetal resins
40. Polyether resins—e.g. polyvinyl ether resins
41. Polyvinyl formal resins
42. Rosin derivatives—e.g. esters of rosin, copal, rosin acids or rosin modified by hydrogenation, polymerization isomerization or disproportionation with glycerol, pentaerythritol or other polyhydric alcohols
43. Maleic/fumaric condensate resins—e.g. maleic or fumaric acid/anhydride adducts on rosin or modified rosins, their esters with glycerol, pentaerythritol or other polyhydric alcohols
44. Silicone resins and polymers
45. Urea resins—e.g. urea-formaldehyde
46. Xylene-formaldehyde resins
47. Natural gums/resins—e.g. accoroides, arabic, benzoin, copals, damar, elemi, gamboge, karaya, mastic, rosin, sandarac, shellac and tragacanth
48. Acrylic polymers and copolymers—e.g. polyacrylic acid, polyacrylamide, polyacrylonitrile, poly(methyl methacrylate) and poly(ethyl acrylate/butyl acrylate)
49. Cellulose ethers—e.g. hydroxyethyl cellulose and sodium carboxymethyl cellulose
50. Cellulose esters—e.g. methyl cellulose
51. Hydrocarbon resins—e.g. petroleum resins
52. Polyamide resins
53. Rubbers—e.g. natural rubber, butyl, rubber, nitrile rubber, polychloroprene, rubber/oil emuline and polyurethane rubber and cyclized rubber resins
54. Vinyl polymer and copolymers other than those already mentioned—e.g. poly(vinyl acetate), poly(vinyl alcohol), poly(vinyl butyral), poly(vinyl pyrrolidone), poly(vinyl acetate/vinyl chloride) and poly(vinyl acetate/acrylate) and
55. Natural drying oils, with or without metal accelerators—e.g. linseed oil and tung oil and mixtures of them.

The concentration of the solution in which the fungicide is applied will depend largely on the method of application and the duration of protection desired. It will appear from data below that phytotoxicity is not a significant factor affecting the maximum concentration at which the materials can be used, so, not withstanding their comparative cheapness, the maximum levels are largely a question of economics. Minimum concentrations are of course determined by the relative effectiveness of the fungicides.

Most arable crops are sprayed at 200 or so liters/ha. The preferred UK commercial rate is 1.25 g/liter for metabisulphite (the active compound used at highest level), i.e. 0.125% concentration and 250 g/ha. Apple trees and the like are sprayed at up to 2,000 liters/ha, (i.e. ten times as much liquid sprayed on a given area of crop) and a similar effect would be expected with the same level of metabisulphite per unit area but at one-tenth of the concentration (0.125 g/liter). At the other extreme, an aircraft or spinning disc (controlled droplet application or CDA sprayer) may use only 10 liters/ha. At these levels control can often be obtained satisfactorily with 20 to 80% or with 100% of the usually applied active ingredient per unit area (50 to 200 or 250 g/ha, i.e. at 10 liters/ha, 5 to 20 or 25 g/liter or 0.5 to 2 or 2.5%). However, the invention contemplates that the materials may be applied at from 5 grams to 2.5 kg per hectare of crop and may be applied in from 10 liters to 2,000 liters of water per hectare. On a v/v basis the addition of a coating material such as di-1-p menthene and its polymers at 0.05–2.5% and a surface active agent such as nonyl phenol ethylene oxide condensate at 0.01 to 0.25% in the final spray solution will improve performance.

For stored products, the volume of liquid needed to treat a tonne of harvested crop varies greatly, depending on the nature of the crop and the period over which protection is desired, and consequently the concentration of the active ingredient may vary from 1 to 100 g/l (0.1 to 10%).

The degree of control achieved at any concentration is strongly influenced by (a) fungal pressure-suitability of conditions for fungal growth (b) time between spraying and assessment.

Fungal pressure may vary results by more than a factor of 10 and for farming use the levels chosen are those which will deal with significant infection pressure. This, for a commercial mixture of all three materials, could be:

| | g/ha |
|---|---|
| Sodium metabisulphite | 500–1500 |
| Sodium propionate | 500–1500 |
| Potassium sorbate | 100–1000 |

As to time from spraying to assessment, under field conditions substantially higher levels are needed for a control of around four to six weeks (as would be desirable commercially) than for seven to fourteen days control. The rates given above reflect a useful commercial range based on present costs of chemicals and crops. Lesser control may be achieved at rates as low as one-tenth of a suitable commercial rate. It must be borne in mind that a "suitable" commercial rate will vary with the values of the crop and this itself can change dramatically.

As mentioned above, most crop spraying from the ground is carried out at around 200 liters per hectare, but can go to 2000 liters per hectare in crops such as apple and citrus trees. Under these conditions it is safe to the crop to use the "commercial" rates indicated so that the concentration of the spray is not decreased as water levels are raised from 200 to 2000 liters per ha.

Alternatively, aerial spraying and controlled droplet application may be used to spray at around 10 liters to the hectare. It is crop safe to use the "commercially" indicated rates per ha at these water levels and control may also be obtained by maintaining the same concentrations of active materials as is obtained at 200 l/ha (which may represent a times 20 decrease in the level of fungicide applied per ha).

The following non-limiting examples, which include comparative data and phytotoxicity test results, illustrate the process and compositions of the present invention.

EXAMPLE 1

Formulations containing:

| | | |
|---|---|---|
| 1 | sodium metabisulphite | 0.03% w/v |
| 2 | sodium propionate | 0.03% w/v |
| 3 | potassium sorbate | 0.03% w/v |
| 4 | sodium metabisulphite + | 0.03% w/v |
| | sodium propionate | 0.03% w/v |
| 5 | sodium metabisulphite + | 0.03% w/v |
| | potassium sorbate | 0.03% w/v |
| 6 | sodium propionate + | 0.03% w/v |
| | potassium sorbate | 0.03% w/v | were made up in water.

Each formulation additionally contained 0.25% v/v of di-1-p-menthene and 0.025% v/v of nonyl phenol ethylene oxide condensate as a surface-active agent.

A formulation (7) containing the di-1-p-menthene and nonyl phenol ethylene oxide condensate but lacking any of the fungicidally active materials contained in formulations 1–6 was prepared as a control material.

These seven formulations were applied to spring barley (variety Triumph) when powdery mildew (*Erisiphe graminis*) could first be detected. Scoring (assessment) was carried out two weeks after spraying on a scale or 0% (which represented no control, as with formulation 7, which was identical with results on unsprayed plants) to 100% (complete control of mildew).

The results were then compared for the actual control of formulations 4, 5 and 6 against the expected performance from the addition of the results of the appropriate two formulations selected from formulations 1, 2 and 3.

| | 1 | 2 | 3 | 4 (1 + 2) | 5 (1 + 3) | 6 (2 + 3) |
|---|---|---|---|---|---|---|
| ACTUAL Control (%) | 40 | 30 | 25 | 100 | 90 | 85 |
| EXPECTED (by addition) | — | — | — | 70 | 65 | 55 |

There is thus an improvement in mildew control of some 50% by using any two materials in mixture in comparison with what is expected by the addition of their individual performances.

EXAMPLE 2

Control of Botrytis ("grey mould") in harvested strawberries

Plastic supermarket packs each contain twenty strawberries (5 replicates) were exposed to infection by placing half an infected strawberry in the centre of each pack. After six days packs were scored from 0 to 10 (no control to 100% control of botrytis) in comparison with unsprayed strawberries.

| A1 | A2 | A3 | A4 | A5 | A6 |
|---|---|---|---|---|---|
| 4 | 2 | 1 | 6 | 3 | 2 |

(application was as a fine mist spray)

| | A1 + A3 | A1 + A2 | A2 + A3 |
|---|---|---|---|
| Expected Control (by addition) | 5 | 6 | 3 |
| Measured Control | 7 | 9 | 5 |

| | A4 + A6 | A4 + A5 | A5 + A6 |
|---|---|---|---|
| Expected Control (by addition) | 8 | 9 | 5 |
| Measured Control | 9.5 | 10 | 7 |

In the foregoing, the solutions were as defined:

| | | Grams/Liter |
|---|---|---|
| A1 = | Sodium metabisulphite | 1.0 |
| A2 = | Sodium propionate | 1.0 |
| A3 = | Potassium sorbate | 1.0 |
| A4 = | Sodium metabisulphite | 5.0 |
| A5 = | Sodium propionate | 5.0 |
| A6 = | Potassium sorbate | 5.0 |

The spray solution contained a wetting agent (nonyl phenol ethylene oxide condensate, 0.025% v/v) and coating agent (di-1-p-menthene, 0.25%).

EXAMPLE 3

Phytotoxicity Testing

For long-term storage high levels of active ingredient are required. To check that there was no fruit damage, strawberries, oranges, lemons, potatoes and celery were sprayed with a formulation containing

| Na metabisulphite | 5% w/v |
|---|---|
| Na propionate | 5% w/v |
| Potassium sorbate | 5% w/v | in water containing 0.025% v/v nonyl phenol ethylene oxide condensate and 0.25% di-1-p-menthene.

No fruit damage resulted, making it possible to use high levels of materials to obtain longer persistence. Strawberries, oranges, lemons and potatoes were sprayed with 10% w/v of sodium metabisulphite or sodium propionate or potassium sorbate in the same wetter/coating system. No damage resulted with any of the materials.

EXAMPLE 4

Control of powdery mildew on flag leaf and second leaf of Natasha spring barley. The additives and concentrations are as defined below.

Plants were sprayed at 220 liters/ha at full flag leaf emergence. Flag and first leaf were scored for mildew control after twenty-eight days. Plants were scored from 0 to 10 (no control to 100% control) in comparison with untreated (unsprayed) plants.

| A1 | A2 | A3 | A4 | A5 | A6 |
|---|---|---|---|---|---|
| 4 | 2 | 1 | 6 | 5 | 2 |

| | A1 + A3 | A1 + A2 | A2 + A3 |
|---|---|---|---|
| By mathematical addition | 5 | 6 | 3 |
| Actual | 8.5 | 10 | 5 |

At higher levels

| | A4 + 6 | A4 + A5 | A5 + A6 |
|---|---|---|---|
| By addition | 8 | 10 | 7 |
| Actual | 10 | 10 | 9.5 |

There was no crop damage at high levels.
The solutions here were as follows:

| | | Grams/Hectare |
|---|---|---|
| A1 = | Sodium metabisulphite | 500 |
| A2 = | Sodium propionate | 500 |
| A3 = | Potassium sorbate | 500 |
| A4 = | Sodium metabisulphite | 2000 |
| A5 = | Sodium propionate | 2000 |

-continued

A6 = Potassium sorbate 2000

Plants were sprayed at 200 l/ha in water containing 0.25% v/v of di-1-p-menthene and 0.025% nonyl phenol ethylene oxide condensate.

"Untreated" plants were sprayed with the di-1-p-menthene/nonyl phenol ethylene oxide condensate only. These were also compared with unsprayed plants. No fungicidal action could be detected from the level of wetting agent/coating material (di-1-p-menthene) used.

EXAMPLE 5

Persistence of control of powdery mildew in Natasha spring barley

| Weeks from spraying | 1 | 2 | 3 | 4 | 5 | 6 | 7 |
|---|---|---|---|---|---|---|---|
| Formulation I | 0 | 0 | 1 | 1 | 2 | 4 | 5 |
| Formulation II | 0 | 0 | 0 | 1 | 1 | 2 | 3 |
| Formulation III | 0 | 0 | 0 | 0 | 1 | 1 | 2 |
| Untreated (surfactant + coating only, no fungicide) | 1 | 2 | 5 | 8 | 11 | 18 | 27 |

(assessment as % disease cover flag/first leaf)

There was no phytotoxic damage in any plants. Plants were also sprayed with the coating/surfactant only. No discernible control of fungi resulted in comparison with unsprayed plants. The formulations were:

| | Sodium metabisulphite | Grams/HA Na propionate | Potassium sorbate |
|---|---|---|---|
| Formulation I | 250 | 250 | 100 |
| Formulation II | 500 | 500 | 250 |
| Formulation III | 1000 | 1000 | 500 |

Sprayed at 200 liters per hectare.

Spray solution contained "wetter" (nonyl phenol ethylene oxide condensate 0.025%) and a coating material (di-1-p-menthene, 0.25% v/v).

EXAMPLE 6

Long Term Storage Test

To obtain long term disease control requires a high initial application of a chemical as the concentration tends to decrease with time and eventually is not sufficient to control infection.

At high levels an initial 100% control may be obtained with a single active ingredient so that it is not possible to improve performance and demonstrate synergism. We have therefore looked for synergism as the effective control declines with time.

Oranges were inoculated with spores of Penicillium blue mould (common storage mould of citrus) after different treatments. They were stored at room temperature (18° to 20° C.) in boxes. At each assessment a fresh inoculation of Pencillium spores was made.
Scoring 0=No Control
Scoring 10=100% Control.

| Weeks | Sodium metabisulphite 2.5% | Na propionate 2.5% | Na metabisulphite 2.5% + Na proportionate 2.5% | Expected (by addition) |
|---|---|---|---|---|
| 2 | 10 | 10 | 10 | 10 |
| 4 | 10 | 7 | 10 | 10 |
| 6 | 6 | 3 | 10 | 9 |
| 8 | 4 | 1 | 10 | 5 |
| 10 | 1 | 0 | 9 | 1 |
| 12 | 0 | 0 | 8 | 0 |

EXAMPLE 7

Phytotoxicity Testing

Solutions of the active ingredient were made up in 0.025% v/v nonyl phenol ethylene oxide condensate (wetter) and 0.25% v/v di-1-p-menthene (coating).

| Active Ingredients | (% w/v) |
|---|---|
| 1 Sodium metabisulphite | 5 |
| 2 Sodium propionate | 5 |
| 3 Potassium sorbate | 5 |
| 4 Sodium metabisulphite | 2.5 |
| Sodium propionate | 2.5 |
| Potassium sorbate | 2.5 |

These were sprayed onto
(a) Flag leaf of emerged Brock winter wheat
(b) Flag leaf of emerged Triumph spring barley
(c) Oil seed rape (Bienvenu) - full flowering
Water volumes - 220 liters per hectare.
Assessment at 24 hours, 7 days and 14 days: No damage observed.

I claim:

1. A method of combatting fungi on plant material comprising applying to said plant material a synergistic effective amount of a fungicidal composition comprising from about 0.0125% to about 2.5% on a w/v basis of non-toxic water-soluble metabisulfite and from about 0.0125% to about 2.5% on a w/v basis of non-toxic water-soluble propionate salt.

2. A method as claimed in claim 1 wherein said fungicidal composition comprises sodium metabisulphite and sodium propionate and further comprises potassium sorbate.

3. A method as claimed in claim 1 wherein the fungicidal composition further comprises 0.05 to 2.5% on a v/v basis of at least one coating agent and 0.01 to 0.25% on a v/v basis of at least one surface-active agent.

4. A method as claimed in claim 3 wherein said coating agent comprises di-1-p-menthene, polymer of di-1-p-menthene, or mixture of di-1-p-menthene and polymer of di-1-p-menthene, and said surface-active agent comprises at least one condensate of nonylphenol ethylene oxide.

5. A method as claimed in claim 1 wherein said plant material comprises harvested fruit or vegetables, and said metabisulfite and said propionate salt are applied in the form of an aqueous solution, the concentration of each in said aqueous solution being in the range of about 1 to about 100 g/l.

6. A method as claimed in claim 1 wherein said plant material comprises growing plants and said metabisulfite and said propionate salt are each applied at a rate in the range from about 5 g to 2.5 kg per hectare.

7. A method as claimed in claim 1 wherein said plant material comprises growing plants, said metabisulfite and said propionate salt are applied in the form of an aqueous composition, and said aqueous composition is applied at a rate of about 10 to about 2000 liters per hectare.

8. A method as claimed in claim 1 wherein said plant material comprises growing plants, said fungicidal compounds being applied in the form of an aqueous composition, said aqueous composition being applied at a rate of about 10 to about 1000 liters per hectare.

9. An aqueous fungicidal composition comprising a synergistic mixture of from about 0.0125% to about 2.5% on a w/v basis of non-toxic water-soluble metabisulfite and from about 0.0125% to about 2.5% on a w/v basis of non-toxic water-soluble propionate salt.

10. A composition as claimed in claim 9 further comprising 0.05 to 2.5% on a v/v basis of at least one coating agent and 0.01 to 0.25% on a v/v basis of at least one surface-active agent.

11. A composition as claimed in claim 9 further comprising 0.05 to 2.5% on a v/v basis of di-1-p-menthene, polymer of di-1-p-menthene or a mixture of di-1-p-menthene and polymer of di-1-p-menthene and 0.01 to 0.25% on a v/v basis of at least one condensate of nonylphenol ethylene oxide.

12. An aqueous fungicidal composition comprising a synergistic mixture of from about 0.1% to about 10% on a w/v basis of non-toxic water-soluble metabisulfite and from about 0.1% to about 10% on a w/v basis of non-toxic water-soluble propionate salt.

13. A composition as claimed in claim 12 further comprising 0.05 to 2.5% on a v/v basis of at least one coating agent and 0.01 to 0.25% on a v/v basis of at least one surface-active agent.

14. A composition as claimed in claim 12 further comprising 0.05 to 2.5% on a v/v basis of di-1-p-menthene, polymer of di-1-p-menthene or a mixture of di-1-p-menthene and polymer of di-1-p-menthene and 0.01 to 0.25% on a v/v basis of at least one condensate of nonylphenol ethylene oxide.

15. An aqueous fungicidal composition comprising a synergistic mixture of from about 0.0125% to about 2.5% on a w/v basis of sodium metabisulphite, and from about 0.0125% to about 2.5% on a w/v basis of sodium propionate.

16. An aqueous fungicidal composition comprising a synergistic mixture of from about 0.1% to about 10% on a w/v basis of sodium metabisulphite, and from about 0.1% to about 10% on a w/v basis of sodium propionate.

* * * * *